(12) United States Patent
Amirav et al.

(10) Patent No.: US 6,627,454 B2
(45) Date of Patent: Sep. 30, 2003

(54) METHOD AND SYSTEM FOR GAS CHROMATOGRAPHY

(76) Inventors: Aviv Amirav, 5 Hayaar Alley, Hod Hasharon (IL), 45269; Gad Frishman, 49 Shimon Ben-Tsvi Street, Givataim (IL); Nitzan Tzanani, 3a Asherman Street, Tel-Aviv (IL)

( * ) Notice: Subject to any disclaimer, the term of this patent is extended or adjusted under 35 U.S.C. 154(b) by 217 days.

(21) Appl. No.: 09/726,885

(22) Filed: Nov. 30, 2000

(65) Prior Publication Data

US 2002/0054832 A1 May 9, 2002

(30) Foreign Application Priority Data

Nov. 5, 2000 (IL) .................................................. 139475

(51) Int. Cl.[7] ........................ G01N 30/02; G01N 30/26; G01N 30/68
(52) U.S. Cl. ............................. 436/161; 73/23.4; 95/82; 96/101; 422/89; 436/154
(58) Field of Search ............................ 422/89; 436/161, 436/154; 73/23.4, 23.41; 95/82; 96/101

(56) References Cited

U.S. PATENT DOCUMENTS

| | | | | |
|---|---|---|---|---|
| 3,662,604 A | * | 5/1972 | Low et al. | |
| 3,858,435 A | * | 1/1975 | Stevens | |
| 5,153,673 A | * | 10/1992 | Amirav | |
| 5,711,916 A | * | 1/1998 | Riggs et al. | |
| 5,741,711 A | * | 4/1998 | Amirav et al. | |

* cited by examiner

*Primary Examiner*—Jan Ludlow
(74) *Attorney, Agent, or Firm*—Lackenbach Seigel; J. Harold Nissen

(57) ABSTRACT

The invention provides a gas chromatography method for analyzing materials vaporizable in a gas chromatograph system, the method including filling a sample injection device with a sample of the compounds to be analyzed; transferring the sample compounds into an analytical separation column with a transfer gas; passing a carrier gas inside the analytical separation column for time separation of the sample compounds; controlling the temperature of the column for achieving separation of the sample compounds; transferring the vaporized sample compounds eluted from the column into a flame ionization detector; providing the gases required for the operation of the flame ionization detector, and analyzing the data output of the flame ionization detector for analysis of the sample compounds, wherein the gases required for the operation of the gas chromatograph system are produced by water electrolysis. In a modification of the method, the gases required for operation of the gas chromatograph system are produced by water electrolysis without separating the hydrogen from the co-produced oxygen. Gas chromatograph systems for analyzing vaporizable materials are also provided.

20 Claims, 2 Drawing Sheets

METHOD AND SYSTEM FOR GAS CHROMATOGRAPHY

FIELD OF THE INVENTION

The present invention relates to a method and apparatus for gas chromatography. More particularly, the invention relates to an electrolyzer-operated gas-cylinder-free gas chromatograph having a flame ionization detector (GC-FID).

BACKGROUND OF THE INVENTION

Gas chromatography (GC) is a widely used analytical technology that is finding a growing number of applications in the analysis of volatile and semi-volatile compounds. Among the several currently available GC detectors, the flame ionization detector (FID) is the detector most widely used and for the broadest range of applications. The FID is based on the combustion of organic compounds that elute from the GC column in a hydrogen diffusion air flame and the consequent production of charged species from the combustion of the organic compounds. The FID is a highly successful detector due to its robustness, high reliability, high sensitivity, universal carbon-selective detection capability, broad linear dynamic range, fast response, high temperature operation capability and excellent reproducibility. As a result, the FID has become the GC industry's standard detector of choice.

However, both the GC and FID suffer from the major limitation of requiring several high quality gases. This limitation impairs the GC's operational safety, severely limits its transportability and usage outside the laboratory, considerably increases its cost of purchase and use, and reduces its ease of use. As a result, portable GC's are mostly used with a thermal conductivity detector (TCD) that is less sensitive than the FID, suffers from limited temperature operation capability and is subjected to water interference. An alternative detector is the photo ionization detector (PID); however, the PID is too selective for many applications and is not semi-quantitative; it thus is incapable of properly analyzing several important compounds, such as methane or acetone.

A new type of FID has been developed, based on the use of a water electrolyzer, for the production of an unseparated, premixed, oxygen and hydrogen combustible gas mixture. This electrolyzer-powered FID (EFID) is based on a premixed, stoichiometric oxygen and hydrogen flame with a relatively low flow rate of the combustible gas mixture. In addition to a different EFID flame, its operation further requires the reduction of the flame tip diameter to prevent flame flashbacks and the heating of the FID gas exit to avoid water condensation. The EFID, despite its different flame chemistry, serves as a carbon-selective detector like the FID and maintains all the advantages of the FID listed above, with the addition of slightly increased sensitivity. The same EFID electrolyzer has also been used for the operation of a nitrogen and phosphorus detector.

The use of the EFID renders superfluous the use of hydrogen and air gas cylinders in the GC. It also considerably reduces the helium carrier gas consumption, since no helium make-up gas is required for optimal operation of the EFID. However, an inert carrier gas, such as helium, nitrogen or hydrogen, is still required for the operation of the GC injector and as a carrier gas for the analytical separation column. The common perception is that oxygen must be avoided, as it destroys the GC separation column. Furthermore, oxygen is a reactive gas that can react and oxidize the sample compounds in the hot injector. Clearly, the complete removal of all of the gas cylinders from the GC remains an important challenge.

DISCLOSURE OF THE INVENTION

The present invention relates to a gas cylinder-free, GC-EFID system. This system is uniquely based on the use of a water electrolyzer for the provision of substantially all of the gases needed for the operation of a GC-FID system. In the system of the invention, the water electrolyzer produces a stoichiometric oxygen and hydrogen gas mixture. The mixture is used as is, without oxygen removal or any gas separation, as the gas needed for the purge and trap injection system, as the carrier gas in the analytical separation capillary column and as the single gas supply source of the EFID. The result is a gas cylinder-free GC-EFID system having only liquid water as a consumable material and that releases only water vapor into the environment at the small rate of about 10 mg/min. The present invention is based on the realization of several important advantages of water electrolysis as a method for the provision of the total gas supply of gas chromatography systems:

1) Water is a safe, non-toxic, environmentally friendly material.

2) Water is a liquid in abundant, easy, low-cost supply.

3) Water provides, upon its electrolysis, a hydrogen and oxygen gas mixture having a gas volume about 2000 times larger than the volume of the water.

4) Unlike gas, water can be transported, including in airplanes, without the safety issues and constraints relating to compressed or flammable gas.

5) Water electrolysis automatically produces the necessary pressure for delivery of the required flow rate of the gases produced.

6) Water electrolysis is amenable to simple, yet accurate, electronic control of the total gas flow rate by controlling the electrolysis current. In addition, the initial stoichiometric ratio of hydrogen to oxygen in the gas mixture is also inherently ensured. Thus, the water electrolyzer replaces a costly, three-channel electronic flow control.

7) Water electrolysis produces ultra-clean gases without any organic compound impurities.

8) Water electrolysis, without subsequent gas separation, provides the ultimately reliable gas supply device with no moving parts.

9) Water electrolysis, without subsequent gas separation, provides the ultimate low energy consumption, pressurized gas source, compared with any other gas generation source.

10) Water electrolysis, with hydrogen and oxygen separation, can provide both relatively inert hydrogen gas to serve as a GC column carrier gas and oxygen for post-column mixing with the hydrogen for EFID operation.

In accordance with the present invention, there is therefore provided a gas chromatography method for analyzing materials vaporizable in a gas chromatograph system, said method comprising filling a sample injection device with a sample of the compounds to be analyzed; transferring said sample compounds into an analytical separation column with a transfer gas; passing a carrier gas inside said analytical separation column for the time separation of said sample compounds; controlling the temperature of said column for achieving separation of said sample compounds; transferring the vaporized sample compounds eluted from said column into a flame ionization detector; providing the gases required for the operation of said flame ionization detector, and analyzing the data output of said flame ionization detector for analysis of said sample compounds, characterized in that the gases required for the operation of said gas chromatograph system are produced by water electrolysis.

In addition, the invention provides a gas chromatography method for analyzing materials vaporizable in a gas chromatograph system, said method comprising filling a sample injection device with a sample of the compounds to be analyzed; transferring said sample compounds into an analytical separation column with a transfer gas; passing a carrier gas inside said analytical separation column for time separation of said sample compounds; controlling the temperature of said column for achieving separation of said sample compounds; transferring the vaporized sample compounds eluted from said column into a detector; providing the gases required for the operation of said detector, and analyzing the data output of said detector for analysis of said sample compounds, characterized in that the gases required for the operation of said gas chromatograph system are produced by water electrolysis without separating the hydrogen from the co-produced oxygen.

The invention further provides a gas chromatograph system for analyzing vaporizable materials, said system comprising means for filling a sample injection device with a sample of the compounds to be analyzed; means for transferring said sample compounds with a transfer gas into an analytical separation column; means for passing a carrier gas inside said analytical separation column for the time separation of said sample compounds; temperature control means for controlling the temperature of said column for achieving separation of said sample compounds; means for transferring vaporized sample compounds eluted from said column into a flame ionization detector for subsequent detection; means for providing the gases required for the operation of said flame ionization detector, and means for analyzing output data of said flame ionization detector for analysis of said sample compounds, characterized in that the gases required for the operation of said gas chromatograph system are provided by a water electrolyzer.

The invention still further provides a gas chromatograph system for analyzing vaporizable materials, said system comprising means for filling a sample injection device with a sample of the compounds to be analyzed; means for transferring said sample compounds with a transfer gas into an analytical separation column; means for passing a carrier gas inside said analytical separation column for time separation of said sample compounds; temperature control means for controlling the temperature of said column for achieving separation of said sample compounds; means for transferring vaporized sample compounds eluted from said column into a detector for subsequent detection; means for providing the gases required for the operation of said detector, and means for analyzing output data of said detector for analysis of said sample compounds, characterized in that the gases required for the operation of said gas chromatograph system are provided by a water electrolyzer without separating the hydrogen from the co-produced oxygen.

BRIEF DESCRIPTION OF THE DRAWINGS

The invention will now be described in connection with certain preferred embodiments with reference to the following illustrative figures so that. it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic block diagram of the gas cylinder-free GC-FID system of the present invention, and FIG. 2 is a chromatogram of five indicated solvent compounds, at a concentration of 500 ppb (v/v) in air, obtained by utilizing the system of FIG. 1.

DETAILED DESCRIPTION

Figure 1:
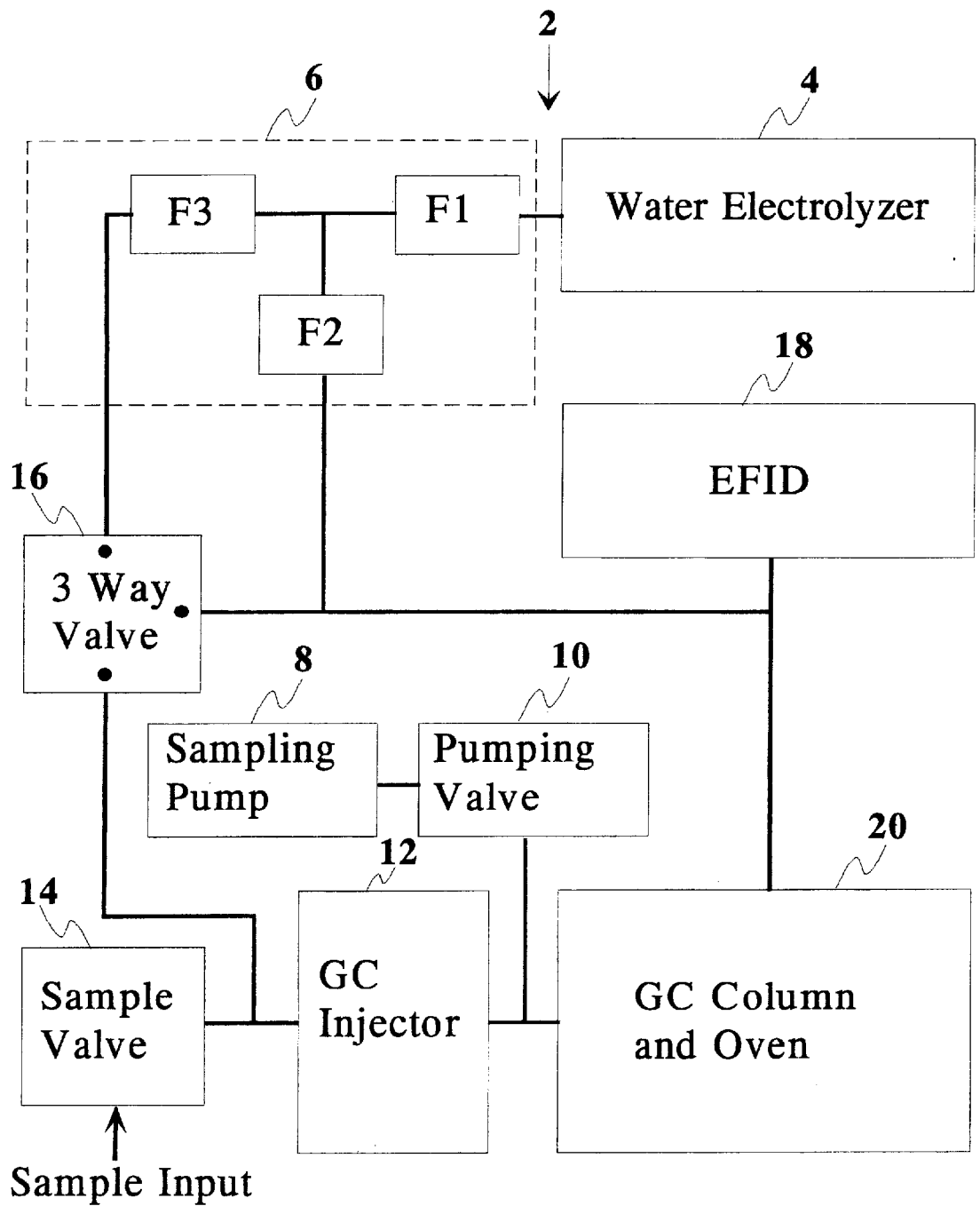

FIG. 1 is a schematic block diagram of the GC-FID system 2 according to the present invention. System 2 is suitably operable for the analysis of volatile organic compounds such as gases and solvents, with boiling points up to about 150° C. In addition, a fast analysis of all the volatile organic compounds, under one minute, with a detection limit of 1 ppb, can be achieved with this system.

The water electrolyzer 4 is compact, being approximately the size of a beverage can. It is operated with 120 ml water and 2A electrolysis current, providing a consumption of 16 ml water per day and the production of 23 ml/min of a stoichiometric hydrogen and oxygen gas mixture. Water electrolyzer 4 has a frit F1 (Mott, 500 ml/min element) at its output, serving both to prevent a flame flashback penetration into the electrolyzer and as a pneumatic, short-term, flow rate stabilizer. The total gas flow rate is regulated electronically by the electrolysis current, acting as an electronic flow control and resulting in good long-term flow rate stability. The combustible gas flow rate is split with a flow splitter 6, constituted by frits F2 and F3 in addition to F1. About 19 ml/min can be passed directly to the EFID for its continuous operation without flameouts.

The analysis cycle begins with the operation of the sampling pump 8 that pumps the sample compounds through pumping valve 10, GC injector 12 and sample valve 14. A home-made check valve, made from Vespel, can be used as the sample valve. The purge and trap GC injector 12 can be based on a 2.5 cm piece of 0.32 mm ID CarbonPLOT column (J&W Folsom, Calif.) inserted inside a stainless steel metal tube having an ID of 0.53 mm and and OD of 0.73 mm (Restek, Bellefonte, Pa.) that serves to heat the CarbonPLOT sample trapping column. Upon the operation of the sampling pump 8, the sampled air is pumped through the CarbonPLOT trapping column and the organic compounds are adsorbed and retained in it. During the step of sample trapping, the 3-way valve 16 diverts all of the combustible gas mixture to the EFID 18.

The second step in the analysis cycle begins with the closure of the pumping valve 10 to stop the air sampling. The 3-way valve 16 is then connected to the GC injector 12 and a 4 ml/min hydrogen and oxygen gas mixture flows through the trapping column (GC injector 12) that is subsequently heated to about 140° C. by a 5A heating current for 2–3 seconds, for thermal desorption purging of the sample compounds. During this stage, the sample compounds are swept by the carrier gas into the analytical separation column. For GC separation, a 1.5 meter, 0.32 mm ID column, inserted inside a stainless steel metal tube having an ID of 0.53 mm and OD of 0.73 mm (SilcoSteel coated transfer line tube, Restek, Bellefonte, Pa.) can be used. The separation column can be based on the use of a PoraBOND PLOT column (Varian-Chrompack, Middelburg, The Netherlands) that utilizes a porous layer of divinylbenzebe as the adsorbing material.

In the third step of the analysis cycle, the gas chromatography separation was initiated. For temperature programming of the separation column, the column was heated to 140° C. by up to 2A direct current heating. The hydrogen and oxygen gas mixture serves as the carrier gas, having a 4 ml/min column flow rate. The column output gas is combined with the 19 ml/min auxiliary gas mixture that is fed directly from the water electrolyzer 4 and is then entered into the EFID 18, where it serves as the total EFID combustible gas mixture. The organic compounds that eluted from the GC column 20 are detected by the EFID 18, and the resulting chromatogram is processed by standard software in a computer or integrator (not shown). A home-made EFID 18, that has its flame tip biased by +50V from an external power supply, may be used. The charge collector of the EFID is connected to a standard FID current amplifier, taken from a Carlo Erba Vega GC-FID system. The EFID insulating spacers are made from Teflon, while the outer body is constructed from 316 stainless steel and the upper gas exit portion from aluminum. The heater of the EFID can be a home-made heating element, having an OD of 1.6 mm, with Kanthal heating wire that provides about 8 Watts. This power is sufficient to heat the EFID 18 to over 150° C. The flame tip used can be based on a modified Hewlett-Packard FID flame tip, with a nozzle diameter of 0.28 mm. A Vespel part serves as the support for the GC, purge and trap, pneumatics and electrical contacts. The latter is thermally connected to the heated EFID via three aluminum rods. Thus, while the EFID 18 is at 150° C., the check valve and GC inlets are at 80° C. The total average energy consumption of this system, operated for an analysis cycle time of 1 minute, is about 20 Watts, making it amenable to, and compatible with, field battery operation.

While the above-described system 2 is a small-size, gas cylinder-free GC-EFID system designed for field applications, clearly the same principles can be applied for the conversion of a standard laboratory GC-FID system into a gas cylinder-free GC-EFID. In a standard gas analysis, the purge and trap system could be replaced by a standard sampling loop, while the check valve could be replaced by a gas sampling valve. Standard liquid injection systems can also be converted into gas cylinder-free GC-EFID operations, but preferably only in the cold on-column or splitless modes of operation, unless the electrolyzer provides more gases for the split exit. The septum purge flow should be minimized in that mode.

The most significant limitation of the gas cylinder-free GC-EFID system 2 is its lower and limited column operation temperature. Clearly, the use of oxygen is undesirable in gas chromatography, and its users are often requested to use special oxygen traps to remove even trace amounts of oxygen from the carrier gas. On the other hand, modern capillary columns are designed for low bleed at high temperatures and thus should be more oxygen-tolerant than commonly perceived. Furthermore, in the analysis of relatively volatile compounds, the adverse effect of potential oxygen reaction with the sample compounds is also minimized at the required relatively low temperatures of the injector and column. It was found that a standard dimethylsiloxane adsorption film can tolerate oxygen in air up to about 200° C. for an extended period of time, and without noticeable column deterioration. With the divinilbenzene phase in the PoraBOND column, the upper limit was found to be 140° C., utilizing the electrolyzer-produced oxygen and hydrogen gas mixture. This temperature limitation still enables analysis of the full range of gases, solvents, volatile organic compounds and even a small portion of the more volatile compounds among the semi-volatile group of organic compounds. The dimethylsiloxane phase was found to be satisfactory for the system 2, but it was not optimal for the proper retention and separation of solvents, due to its low retention power. Thus, the PoraBOND column is preferred, despite its lower temperature compatibility.

For higher column temperature GC-EFID operation, the hydrogen and oxygen should be separated so that pure hydrogen will serve as the injection and column carrier gas. In contrast, however, to the currently used GC systems, the use of the EFID uniquely removes the need for a large flow rate of clean air; the co-produced oxygen can be mixed with the hydrogen after its elution from the GC column, to again form a stoichiometric hydrogen and oxygen gas mixture as required for the operation of the EFID.

The analysis of gases and volatile organic compounds is, in many cases, performed with splitless sample injection. In contrast, the analysis of semi-volatile compounds requires split-splitless or split injection, in order to eliminate the tailing solvent signal. Split or split-splitless injection requires a much higher gas flow rate, in order to sustain the additional high split gas flow rate. As a result, for semi-volatile compound analysis with split or split-splitless injection, a larger water electrolyzer is required, with or without hydrogen and oxygen separation.

Figure 2:
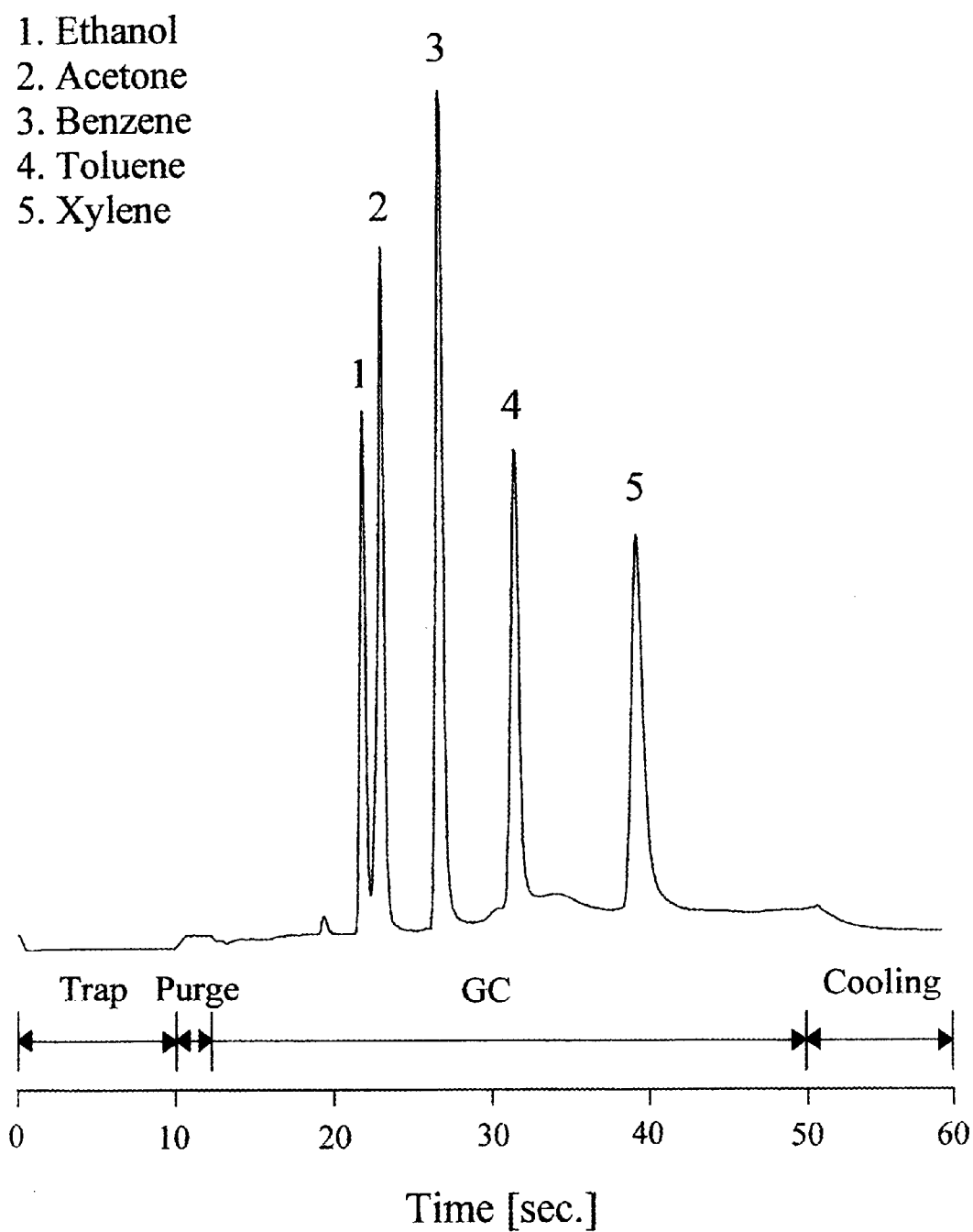

In FIG. 2, there is shown a fast chromatogram of ethanol, acetone, benzene, toluene and ortho xylene. These compounds were dissolved in trimelitate at liquid concentrations that produced 500 ppb (v/v) head space concentrations in air. As illustrated at the bottom of the figure, the head space was sampled at a 30 ml/min sampling flow rate for 10 seconds, so that 5 ml air were analyzed. Immediately after the 10 seconds sampling time, the pumping valve 10 of FIG. 1 was closed, the carrier gas of non-separated hydrogen and oxygen gas mixture entered the trap, and the three-second desorption period began. After these three seconds, the trap heating stopped and the GC column heating began, lasting for 37 to 50 seconds from the beginning of the analysis. The analysis cycle ended with 10 seconds of cooling that could be used for additional sample trapping. Consequently, FIG. 2 demonstrates a full analysis cycle time of less than one minute, with low ppb detection limits for the full range of organic solvents and without any gas cylinders.

The EFID short-term noise was found to be less than the equivalent of 0.1 ppb (about 20 femtoAmpere). On the other hand, the column bleed chemical noise due to the action of the oxygen in the carrier gas, as well as other types of chemical noise, restricted the detection limit to about 1–2 ppb. The small hump seen in FIG. 2 at 30–35 seconds relates to a yet unknown origin in the sample itself, but it is absent with lower concentration samples. With a temperature program up to 110° C., the column-produced chemical noise was significantly reduced and sub-ppb detection limits were achieved. Under these conditions, however, the compound toluene was the last to elute compounds and xylene could not be properly analyzed. The CarbonPLOT trapping column was found to be an effective trap for all the sample solvent compounds for up to 10 ml sample volumes. Above this air sample volume, the more volatile organic compounds began to penetrate the trap. The sample trap was heated up to 170° C., but only about 100° C. were needed for fill desorption of the sample compounds. The PoraBOND column was also tested as a trap, but it was found to be inferior to the CarbonPLOT trap, due to its lower capability of trapping the more volatile compounds and its higher bleeding level with oxygen.

In the chromatogram shown in FIG. 2, a 1.5 meter column was used with a 0.32 mm ID PoraBOND column. The separation power of this column was independently tested under isothermal conditions, and it was found to be characterized by 1200 separation plates, as it exhibited a ratio of elution time to peak width of close to 16. This separation capability seems sufficient for the analysis of simple volatile organic compounds. If increased separation power is needed, a longer column, such as a 15 meter 0.53 column, that should have over 20,000 separation plates, can be used. A standard 30 meter 0.25 mm ID column can also be used with increased column head pressure that could be provided by the water electrolyzer, but the analysis time will be considerably increased.

In FIG. 2, the complete separation of five solvent compounds is demonstrated; their time-integrated areas enable their quantitative determination, as is commonly accomplished with gas chromatography. It is recognized that the sum of these amounts represents the total organic matter in the sample. However, with the utilization of the same system, the separation column can be replaced with a non-adsorption transfer line and a non-adsorption sample loop can be used for achieving even faster total organic compound analysis, without GC separation, with only these two minor modifications. Fast, total organic compound (TOC) determination was successfully tested, and 1 ppm TOC was easily measured, using this method.

While the use of a water electrolyzer has been described for the operation of a gas chromatograph equipped with an EFID as its detector, other GC detectors can also be used, such as a photo ionization detector (PID), a thermal conductivity detector (TCD), a mass spectrometer detector (MSD), or most other available GC detectors that can use electrolyzer-produced gases as their gas source. This is so since the water electrolyzer provides a few advantages over its alternatives. In comparison with standard hydrogen generators, the water electrolyzer is far smaller, lighter and requires much less energy, due to the elimination of the oxygen and hydrogen separation step and high hydrogen pressure stabilization. Furthermore, the stoichiometric hydrogen and oxygen ratio enables the production of a flame with the smallest amount of output gases, i.e., pure water vapor, which can be separated from other flame co-produced gas species. For certain applications, such as GC-MS, it is beneficial to catalytically convert the hydrogen and oxygen back to water in the vacuum system for its easier pumping by chemical adsorption. In comparison with air-powered GC, the water electrolyzer automatically provides the required column head pressure without any bulky and noisy air compressor; in addition, the quality and cleanliness of its generated gas is much better.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A gas chromatography method for analyzing materials vaporizable in a gas chromatograph system, said method comprising:

filling a sample injection device with a sample of the compounds to be analyzed;

transferring said sample compounds into an analytical separation column with a transfer gas;

passing a carrier gas inside said analytical separation column for time separation of said sample compounds;

controlling the temperature of said column for achieving separation of said sample compounds;

transferring the vaporized sample compounds eluted from said column into a flame ionization detector;

providing the gases required for the operation of said flame ionization detector, and analyzing the data output of said flame ionization detector for analysis of said sample compounds, characterized in that the transfer gas, the carrier gas and the gases required for operation of the flame ionization detector are produced by water electrolysis.

2. A gas chromatography method for analyzing materials vaporizable in a gas chromatograph system, said method comprising:

filling a sample injection device with a sample of the compounds to be analyzed;

transferring said sample compounds into an analytical separation column with a transfer gas;

passing a carrier gas inside said analytical separation column for time separation of said sample compounds;

controlling the temperature of said column for achieving separation of said sample compounds;

transferring the vaporized sample compounds eluted from said column into a detector;

providing the gases required for the operation of said detector, and analyzing the data output of said detector for analysis of said sample compounds, characterized in that the transfer gas, the carrier gas and the gases required for operation of the detector are produced by water electrolysis without separating the hydrogen from the co-produced oxygen.

3. The method according to claim 1, wherein said water electrolysis provides a hydrogen and oxygen gas mixture without separating the hydrogen from the co-produced oxygen.

4. The method according to claim 1, wherein said water electrolysis provides separated hydrogen and oxygen gases that are recombined prior to their transfer into said flame ionization detector, for its operation with a hydrogen and oxygen gas mixture.

5. The method according to claim 1, wherein said gas chromatography system also serves to determine the total content of organic compounds in air or a gaseous sample.

6. The method according to claim 1 or claim 2, wherein said sample injection device is operable as a sample loop filled with a gaseous sample.

7. The method according to claim 1 or claim 2, wherein said sample injection device is a standard liquid injection gas chromatography injector.

8. The method according to claim 1 or claim 2, wherein said sample injection device is based on gas phase or airborne sample adsorption, followed by sample injection through sample thermal desorption.

9. The method according to claim 1 or claim 2, wherein said gas chromatograph utilizes materials that are oxygen-stable at the required analysis temperature.

10. A gas chromatograph system for analyzing vaporizable materials, said system comprising:
    means for filling a sample injection device with a sample of the compounds to be analyzed;
    means for transferring said sample compounds with a transfer gas into an analytical separation column;
    means for passing a carrier gas inside said analytical separation column for time separation of said sample compounds;
    temperature control means for controlling the temperature of said column for achieving separation of said sample compounds;
    a flame, ionization detector,
    means for transferring vaporized sample compounds eluted from said column into said flame ionization detector for subsequent detection;
    means for providing the gases required for the operation of said flame ionization detector;
    means for analyzing output data of said flame ionization detector for analysis of said sample compounds, and,
    a water electrolyzer,
    characterized in that the transfer gas, the carrier gas and the gases required for operation of the flame ionization detector are provided by said water electrolyzer.

11. A gas chromatograph system for analyzing vaporizable materials, said system comprising:
    means for filling a sample injection device with a sample of the compounds to be analyzed;
    means for transferring said sample compounds with a transfer gas into an analytical separation column;
    means for passing a carrier gas inside said analytical separation column for time separation of said sample compounds;
    temperature control means for controlling the temperature of said column for achieving separation of said sample compounds;
    a detector,
    means for transferring vaporized sample compounds eluted from said column into said detector for subsequent detection;
    means for providing the gases required for the operation of said detector;
    means for analyzing output data of said detector for analysis of said sample compounds;
    a water electrolyzer,
    characterized in that the transfer gas, the carrier gas and the gases required for operation of the detector are provided by said water electrolyzer without separating the hydrogen from the co-produced oxygen.

12. The system according to claim 10, wherein said water electrolyzer provides a hydrogen and oxygen gas mixture without separating the hydrogen from the co-produced oxygen.

13. The system according to claim 10, wherein said water electrolyzer provides separated hydrogen and oxygen gases and further comprising means for recombining said hydrogen and oxygen gases that are recombined prior to their transfer into said flame ionization detector, for its operation with a hydrogen and oxygen gas mixture.

14. The system according to claim 10, wherein said system also is operative to determine the total content of organic compounds in air or a gaseous sample.

15. The system according to claim 10 or claim 11, wherein said means for sample injection is constituted by a sample loop filled with a gaseous sample.

16. The system according to claim 10 or claim 11, wherein said means for sample injection is constituted by a standard liquid injection gas chromatography injector.

17. The system according to claim 10 or claim 11, wherein said means for sample injection is constituted by means for as phase or airborne sample adsorption, followed by sample injection through sample thermal desorption.

18. The system according to claim 10 or claim 11, wherein said analytical separation column is an open tubular column coated on its inside with a sample adsorption film or a porous layer.

19. The system according to claim 10 or claim 11, wherein said analytical separation column is a packed column.

20. The system according to claim 10 or claim 11, wherein said analytical separation column is of the type suitable for use with materials that are oxygen-stable at the required analysis temperature.

* * * * *